United States Patent [19]

Fay, Jr.

[11] 4,009,708
[45] Mar. 1, 1977

[54] PULSE RATE RECORDER

[76] Inventor: John J. Fay, Jr., 24 Drake Lane, Levittown, N.Y. 11756

[22] Filed: May 29, 1975

[21] Appl. No.: 581,772

[52] U.S. Cl. .......................................... 128/2.05 P
[51] Int. Cl.² ............................................ A61B 5/02
[58] Field of Search .............. 128/2.05 P, 2.05 E, 128/2.05 N, 2.05 Q, 2.05 R, 2.05 S, 2.05 T, 2.06 F

[56] References Cited

UNITED STATES PATENTS

| | | | |
|---|---|---|---|
| 2,831,479 | 4/1958 | Briskier | 128/2.05 P |
| 2,854,968 | 10/1958 | Wright | 128/2.05 P |
| 3,426,747 | 2/1969 | Herman et al. | 128/2.05 P |
| 3,473,526 | 10/1969 | Herman et al. | 128/2.05 P |
| 3,535,067 | 10/1970 | Lesher et al. | 128/2.05 P |
| 3,807,388 | 4/1974 | Orr et al. | 128/2.05 P X |

Primary Examiner—William H. Grieb
Attorney, Agent, or Firm—Jack D. Slobod

[57] ABSTRACT

A pulse recorder self contained in a wristwatch type case includes a front face having a sweep second hand actuated by an electrical stop watch movement, and a three digit electronic display for the number of pulses counted during the time interval of motion of the second hand. A microphonic or pressure transducer is carried by the back face of the case so as to be pressed into contact with the wrist and is fed to a counter memory driving the display. An initial stop and an angularly moveable stop for the second hand set the time interval for which the hand is to move and provide electrical contacts for enabling the counter only when the hand is in motion.

2 Claims, 3 Drawing Figures

PULSE RATE RECORDER

FIELD OF THE INVENTION

The present invention relates generally to pulse rate transducers adapted to be secured to a wrist. In its particular aspects the present invention relates to a combined interval timer and pulse counter in a wristwatch type case.

BACKGROUND OF THE INVENTION

In view of the prevalence of heart and circulatory problems in our population, there is a need for a portable device by which a person may frequently take his own pulse in order to regulate his activity to safe and possibly exercising levels that do not unduly strain his heart. Since pulse measurements are normally taken by a trained individual holding the wrist of the person, whose pulse is being measured, or in a laboratory by placing a transducer on an individual, it is not generally possible or feasible for an individual to monitor his own pulse rate during usual activities. While some devices in the prior art are known which comprise self contained units in a wrist watch type case for providing either a rough indication of pulse rate, such as U.S. Pat. No. 3,535,067 to Lesher et al. or a signal at the occurence of a predetermined pulse rate such as U.S. Pat. No. 2,854,968 to Wright, such known devices provide neither precise enough nor sufficient information for an individual to properly regulate his level of activity. Furthermore, a device such as provided by Lesher et al., since it has no memory unduly hampered the individual in requiring that he view the device during his activity.

OBJECTS OF THE PRESENT INVENTION

It is an object of the present invention to provide a pulse rate recorder self contained in a wristwatch type case which provides precise measurement of pulse rate.

It is a further object of the present invention to mechanize a pulse rate recorder in such a way that a memory is utilized so that the pulse rate may be determined at the conclusion of an activity.

It is yet another object of the present invention to provide a pulse rate recorder which will count pulses in a time interval of a preselected variable length in order to match the period of measurement with the duration of the individual's activity.

SUMMARY OF THE INVENTION

Briefly, the aforementioned and other objects of the present invention are satisfied by providing in a wristwatch type case an interval timer comprising a stop watch movement including a sweep second hand whose motion is stopped by an angularly adjustable stop. There is further provided in the case an electronic counter memory which is fed by a pulse transducer on the back of the watch case and drives an electronic digital display on the front face of the case. The stop, when contacted by the hand provides an electrical contact for stopping the counting of the counter, thus providing a memory of the number of pulses counted as well as the length of the time interval.

Other objects, features and advantages of the present invention will become apparent upon perusal of the following detailed description of the preferred embodiment thereof when taken in conjunction with the appended drawing wherein.

DETAILED DESCRIPTION

Figure 1:
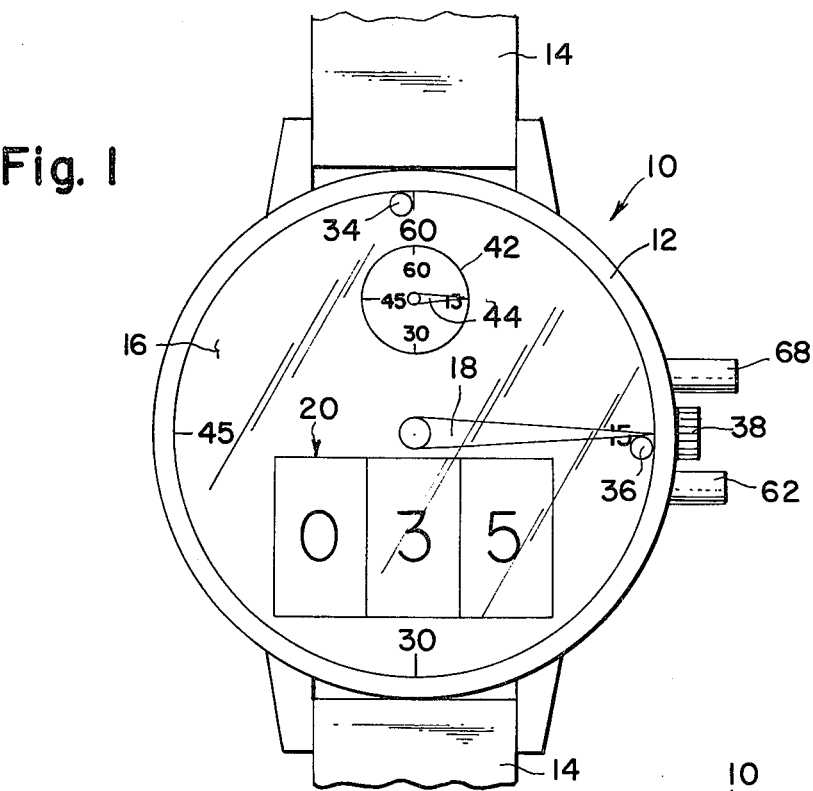
FIG. 1 is a top view of the pulse rate recorder of the present invention.
Figure 2:
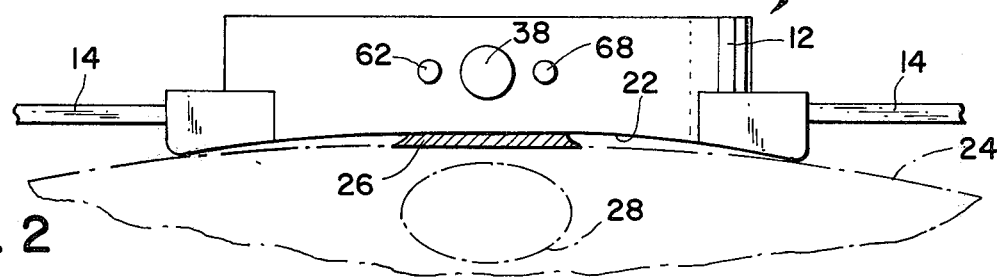
FIG. 2 is a side elevational view from the right of the recorder in FIG. 1.

Referring to FIGS. 1 and 2, the pulse rate recorder 10 of the present invention is self contained in a wristwatch type case 12 having a wristband 14 secured to opposite sides of case 12. Case 12 further has a front face 16, on which is provided a one minute sweep second hand 18 and a three digit electronic display 20, formed for example of light emitting diodes (LED'S), for indicating a pulse count. On the back face 22, of case 12, which is pressed against the wrist 24 of the user, there is carried a transducer 26 which may be either a microphone or a pressure sensor for converting the pulsations of blood in an arterial vessel 28 in wrist 24 to countable electrical pulses for sequentially indexing or incrementing display 20.

Figure 3:
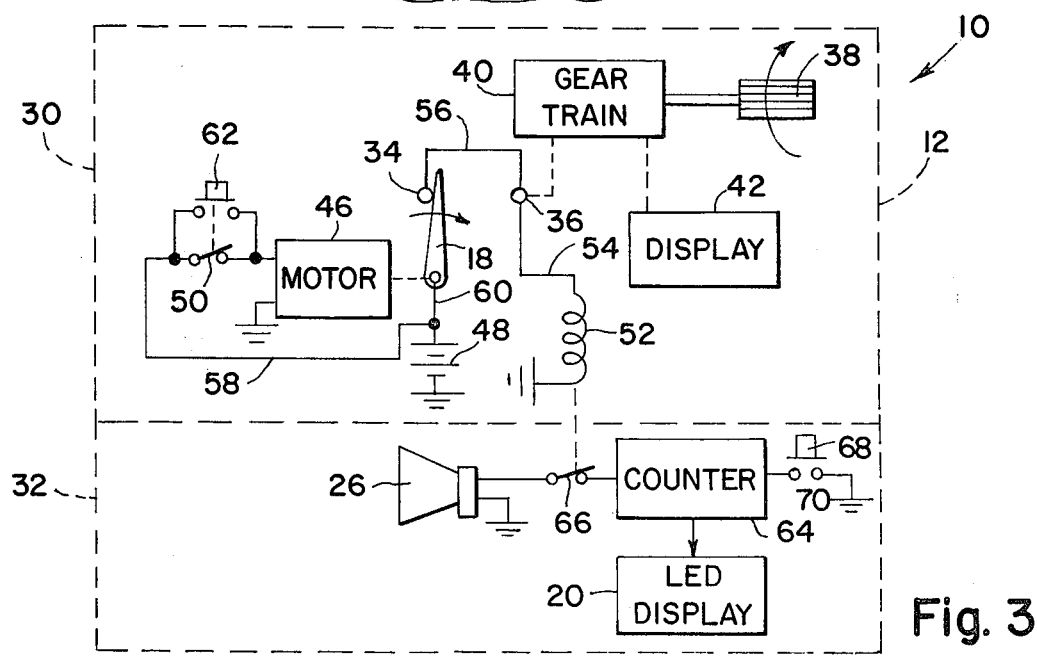
FIG. 3 is a schematic representation of the recorder in FIGS. 1 and 2.

Now referring also to FIG. 3, wherein the contents of case 12 are schematically illustrated, it will be appreciated as the discussion proceeds that the pulse rate recorder 10 of the present invention comprises generally an interval timer 30, including the second hand 18 which runs for a pre-selected length of time and a pulse counter 32 responsive to transducer 26 and including display 20 for recording the number of pulses occurring during the running of timer 30.

Interval timer 30, comprises a type of electrical stop watch movement wherein the end of hand 18 is adapted to be stopped by a pair of mechanical and electrical stops 34 and 36 angularly located around the periphery of front face 16 to define the interval of time which the hand is to run. Stop 34 is fixedly located at the usual zero or sixty second position on face 16, while the angular position of stop 36 is adjustable by means of a winder stem 38 emanating from the side of case 12 which angularly rotates stop 36 via gear train 40. A small circular display 42 including a rotatable pointer arm 44 may also be provided on face 16. Arm 44 is also rotated by stem 38 via gear train 40 to provide an angular indication of the location of stop 36.

Sweep second hand 18 is rotatably driven by an electric motor means 46. A battery 48, having its negative side grounded to case 12, energizes motor means 46, via a normally closed relay contact 50. The corresponding relay coil 52, having one end grounded, is electrically connected at its other end to both stops 34 and 36 by leads 54 and 56. The positive end of battery 48, as well as being connected to contact 50 by lead 58, is also connected to hand 18 by lead 60.

Thus, when hand 18 is in its initial or zero position, in contact with stop 34, the coil 52 is energized, opening the contact 50 to prevent the motor means 46 from being energized to rotate hand 18. For starting the hand 18 in motion there is provided a momentary contact push button switch 62, emanating from the side of case 12 next to winder stem 38. Push button switch 62 is electrically connected bridging relay contact 50 so that when the button of switch 62 is pushed motor means 46 is energized, and hand 18 moves off stop 34, so that coil 52 is no longer energized. Consequently, contact 50 is closed to allow the hand 18 to continue moving until the stop 36 is encountered, where the relay coil 52 is again energized opening contact 50. It should be apparent that relay coil 52 is not energized only when hand 18 is in motion.

Pulse counter 32 comprises an electronic binary coded decimal counter memory 64 which is fed by transducer 26 via another normally closed contact 66 activated by relay coil 52. The counter 64 feeds the digits of display 20 in parallel. Since relay coil 52 is not energized only when hand 18 is in motion, contact 66 is closed only when the hand is in motion to enable the pulse signal from the transducer to increment counter 64. For resetting counter 64 to zero, another momentary contact electric pushbutton switch 68, is provided on the side of case 12 adjacent winder stem 38. Switch 68 is electrically connected between the reset input 70 of counter 64 and ground for resetting the counter upon momentary closure of switch 68.

In the use of the pulse rate recorder 10 of the present invention, the winder 38 is rotated to set stop 36 to determine the number of seconds the hand 18 is to move from its zero position. Counter 64 is then reset by pushing button 68. When it is desired to take a pulse rate measurement, the button 62 is depressed momentarily to start hand 18 in motion. At that time pulses from transducer 26 start to increment counter 64, and the display 20. When hand 18 reaches stop 36, its motion stops and the transducer 26 is disconnected from counter 64 by the action of relay 52. Counter 64 maintains the number of pulses counted until subsequently reset. In determining the pulse rate, the number appearing on display 20, is simply multiplied by the fraction of a minute indicative of the position of hand 18 at stop 36, providing a precise measurement taken over an adjustable length of time.

Having described the preferred embodiment of the invention in great detail, it should be apparent that numberous modifications, additions and ommissions to the details thereof are possible within the spirit and scope of the invention. Accordingly, reference as to the scope of the invention sould be made to the following claims.

What is claimed is:

1. A self contained circulatory pulse rate measuring and indicating device comprising: a case; means carried by said case for securing said case to the wrist of a wearer; said case having a front face and a back face; a pulse transducer carried on said back face for contact with said wrist; a digital counter means within said case; a digital display on said front face driven by said counter means; a sweep second hand on said front face; electric motor means within said casing for drivingly rotating said hand at a predetermined rate, first and second stops angularly disposed about said hand for engagement by said hand when said hand is in predetermined orientations; said first stop being fixedly positioned at one angular position; gear train means for angularly moving said second stop to an adjustable angular position; said hand and said stops forming a portion of a switch means for electrically energizing said motor means and for coupling said transducer means for indexing said counter only when said hand is positioned between said stops.

2. The device of claim 1 wherein said switch means further comprises a normally closed relay having a first contact in series with said motor means and a second contact between said transducer and said counter; said relay having a coil which is energized in response to said hand engaging either of said stops; and further comprising a normally open momentary manual switch bridging said first contact for initiating the movement of said hand.

* * * * *